United States Patent
Kulkarni et al.

(10) Patent No.: US 11,464,425 B2
(45) Date of Patent: Oct. 11, 2022

(54) FLOW SENSING ARRANGEMENT FOR SPIROMETER AND METHOD THEREOF

(71) Applicant: CIPLA LIMITED, Maharashtra (IN)

(72) Inventors: Nandan Kulkarni, Maharashtra (IN); Vidur Malhotra, Maharashtra (IN); Geena Malhotra, Maharashtra (IN); Brinder Ahluwalia, Karnataka (IN)

(73) Assignee: CIPLA LIMITED, Maharashtra (IN)

( * ) Notice: Subject to any disclaimer, the term of this patent is extended or adjusted under 35 U.S.C. 154(b) by 290 days.

(21) Appl. No.: 16/633,890

(22) PCT Filed: Jul. 26, 2018

(86) PCT No.: PCT/IN2018/050490
§ 371 (c)(1),
(2) Date: Jan. 24, 2020

(87) PCT Pub. No.: WO2019/021316
PCT Pub. Date: Jan. 31, 2019

(65) Prior Publication Data
US 2020/0214593 A1    Jul. 9, 2020

(30) Foreign Application Priority Data

Jul. 26, 2017  (IN) .............................. 201721026601

(51) Int. Cl.
*A61B 5/087* (2006.01)
*A61B 5/091* (2006.01)
(Continued)

(52) U.S. Cl.
CPC .............. *A61B 5/087* (2013.01); *A61B 5/091* (2013.01); *A61B 5/0022* (2013.01); *A61B 5/097* (2013.01);
(Continued)

(58) Field of Classification Search
None
See application file for complete search history.

(56) References Cited

U.S. PATENT DOCUMENTS

| 3,504,542 A | 4/1970 | Blevins |
| 4,034,743 A | 7/1977 | Greenwood |
| (Continued) | | |

FOREIGN PATENT DOCUMENTS

| EP | 0627196 A1 | 12/1994 |
| JP | 2011-117444 A | 6/2011 |
| (Continued) | | |

OTHER PUBLICATIONS

International Search Report, dated Dec. 11, 2018 in PCT/IN2018/050490.

(Continued)

*Primary Examiner* — Michael R Bloch
(74) *Attorney, Agent, or Firm* — Knobbe, Martens, Olson & Bear, LLP

(57) ABSTRACT

A flow-sensing arrangement within a spirometer. The arrangement includes a tubular-member for allowing an air-passage along a longitudinal-axis thereof. At-least two disc-shaped air-resistive elements are removably-arranged within the tubular member to resist the air-flow. Each of the resistive-elements include perforations for allowing the air-passage through the resistive-element. At-least two ports extend radially outward through a wall of the tubular member, such that each of the two ports are located within the tubular-member near the resistive-elements to cause determination of at least a pressure-difference there-between.

9 Claims, 5 Drawing Sheets

(a)

(b)

(51) Int. Cl.
    *A61B 5/00*     (2006.01)
    *A61B 5/097*    (2006.01)
    *A61M 16/00*    (2006.01)

(52) U.S. Cl.
    CPC .... *A61B 5/7278* (2013.01); *A61M 2016/0036* (2013.01)

(56) References Cited

U.S. PATENT DOCUMENTS

| | | | |
|---|---|---|---|
| 4,905,709 | A | 3/1990 | Bieganski et al. |
| 5,060,655 | A | 10/1991 | Rudolph |
| 5,522,397 | A * | 6/1996 | Vermaak ................ A61B 5/087 600/533 |
| 6,090,049 | A | 7/2000 | Cha |
| 6,164,142 | A | 12/2000 | Dimeff |
| 2007/0017303 | A1 | 1/2007 | Fujiwara et al. |
| 2009/0064794 | A1 | 3/2009 | Bonassa |
| 2011/0125045 | A1 | 3/2011 | Scholz et al. |
| 2015/0320949 | A1 | 11/2015 | Jaffe |
| 2016/0038056 | A1 | 2/2016 | Johnson et al. |
| 2019/0254534 | A1 * | 8/2019 | Koltowski ........... A61B 5/0205 |

FOREIGN PATENT DOCUMENTS

| | | |
|---|---|---|
| JP | 2015-503388 A | 2/2015 |
| WO | WO 01/042744 A2 | 6/2001 |

OTHER PUBLICATIONS

Written Opinion of the International Searching Authority, dated Dec. 11, 2018 in PCT/IN2018/050490.
European Search Report in European Patent Application No. 18837473.0 dated Apr. 9, 2021.
Japanese Office Action issued in Japanese Patent Application No. 2020-504198 dated Jun. 30, 2021.

* cited by examiner

FLOW SENSING ARRANGEMENT FOR SPIROMETER AND METHOD THEREOF

FIELD OF THE INVENTION

The present disclosure relates to spirometer and in particular relates to assembly and functionality of the spirometer.

BACKGROUND AND PRIOR ART

Pneumotachography, which has been widely used in respiratory organ research can be employed as a measuring method for the measurement of flow rate during the forced exhalation test by the patient/healthy individual. It involves measuring a differential-pressure across the flow path at more than one point and computing the flow rate based on the pressure difference value.

Spirometer, a device based on pneumotachography, comes in various types and employs a variety of technologies to measure breath parameters of a patient. At one end of the spectrum, is the pneumatic and mechanical volume based spirometer that gives a full graph of the complete breath cycle of the user. However such a spirometer is typically very expensive and it is not possible for every patient to have a personal-spirometer at home. At the other end, there are low cost flow sensor based peak flow meters that allow easy measurement of breath-parameters. Yet, many of these lack capability to produce a detailed and complete inhalation and exhalation profile.

An electronic-spirometer sits between the two extremes both on cost of production and on output. The electronic-spirometer is typically much-cheaper to produce than a professional spirometer and it is possible to record the readings electronically, thereby enabling the patient and clinicians to compare the results over time in an easy manner.

There are a few options in the market as far as electronic-spirometers are concerned. They employ a slew of technologies and vary widely on cost and ease of use. In an example, a number of spirometers have been constructed with non-metallic, synthetic fabric resistive elements disposed at the air discharge end of the air tube. However, these devices suffer from either complex construction or unreliable readings. A device by Puritan-Bennett corporation "FS 200 flow sensor" has an elongated hollow plastic tube and a circular air inlet opening at one end. The plastic tube is flared outwardly in the fashion of a bell of a trumpet at the air discharge end. The air discharge opening is covered with an air-resistive fabric and a radially-extending pressure pickoff opening or port through the wall of a plastic tube for a transducer attachment.

A spirometer "MySpiroo®", a Polish product, is a digital spirometer deploying thermal sensing technology and connects to a dedicated mobile app for its data collection, test result reporting and recording of the test data.

Another spirometer "Asthma Monitor AM3 BT" is a Bluetooth-enabled device for measuring critical lung function with comparable accuracy to clinical-grade spirometers. The device sends the data to a smartphone or tablet. This deploys ultrasound sensing methodology to predict the flow-rate and hence generate the complete exhalation and inhalation curve.

U.S. Pat. No. 4,905,709 relates to another spirometer device containing a resistive element, wherein the resistive element is disposed near a sealed end of the air tube and three rectangular air outlet openings are formed through the sidewall of the tube. Although it attempts to produce linear results, it exhibits a complex construction and cleaning process is extremely difficult for repetitive usage.

International publication no WO 01/42744 covering a modified pneumotachometer based spirometer depicts disposable resistive element which can be easily produced and disposed in the form of screens. Further, the design of air tube is such that the fabric is placed in a slant position relative to the axis of the flow inside the tube.

U.S. Pat. No. 6,090,049 discloses a screen-type spirometer with an improved pneumotachometer which has a hollow housing having an annularly shaped ring and a first respiratory tube integrally formed with the annularly shaped ring, and a second respiratory tube which can be engaged with the housing. Both the first and the second respiratory tube can be inserted into a mouth of a person to be examined. Further, the first and second respiratory tubes have a tapered portion which is inclined at 10 degrees respectively in order to stabilize the fluid flow passing there-through.

While a conventional pneumotachometer or flow sensor or mouthpiece containing an integrated bundle of metallized tubes to provide capillary air flow may provide accurate and reliable readings, yet it suffers from a problem that a flow sensor containing a resistive element—which is nothing but a bundle of metallized tubes—of this nature is very costly. Secondly, a sensor of this nature is typically used repeatedly and must be sterilized between uses, thereby affecting the calibration of the flow sensor towards the instrumentation with which it is used. Accordingly, periodic recalibration is required.

Another problem with the usage of the fabric or filter type element is that since the airflow through the fabric (e.g. Puritan-Bennett corporation device) is typically non-uniform across the breadth of airflow, an undesirable non-linear relationship between air flow and air pressure is often resulted Additionally, given the intrinsic difference between the flow properties (turbulent dissipation, flow separation, Reynold's number etc.) at very high and very low ranges of flow rates, these prior-art resistive elements have been only somewhat effective for low airflow rates or for high air flow rates. However, the effectiveness is not met for both the ranges simultaneously. Moreover, the conventional-devices remain a victim of complex-construction and cleaning process.

Further, the deployment of fixed type resistive elements (mesh etc.) creates a difficulty in cleaning of the device and causes microbial contamination. Additionally, as the mesh traps food/dust particles or is subjected to moisture ingress, the resistance of the mesh changes with repetitive usage for long period, thereby impacting accuracy and resulting in malfunctioning.

Another problem is the difficulty in transferring data electronically. Yet another problem with the conventional spirometers is that either they have a battery that needs to be replaced after certain usage, or are required to be permanently connected to a dedicated computer for their operation.

SUMMARY

This summary is provided to introduce a selection of concepts in a simplified format that are further described in the detailed description of the invention. This summary is not intended to identify key or essential inventive concepts of the invention, nor is it intended for determining the scope of the invention.

In an embodiment, the present subject matter describes a tubular-member for allowing an air-passage along a longitudinal-axis thereof. At least two disc-shaped air-resistive elements are removably-arranged within the tubular member to resist the air-flow, such that each of said resistive-elements comprises a plurality of perforations for allowing the air-passage through the resistive-element. At least two ports extend radially outwards through a wall of said tubular member, each of said two ports located within the tubular-member near the resistive-elements to cause determination of at least a pressure-difference there-between.

In an embodiment, the present subject matter relates to an electronic spirometer comprising at least two disc-shaped air-resistive elements removably arranged in an airway and comprising a plurality of hexagonal holes extending between the two faces of each said element, wherein said plurality of holes cover at least 30% of surface-area of each of said faces. At least two hollow tubes are connected to a pressure/temperature sensor. Each of said at least two tubes extend from a designated resistive element in the airway till the sensor to facilitate sensing of air-pressures/temperatures with respect to said at least two elements.

An electronic-module is placed inside the plastic-housing and connected to the pressure-sensor to determine at least one parameter pertaining to the air-flow at least based on a pressure/temperature differential between said two points across the airway.

In an implementation, the electronic-control module or the electronics within the spirometer comprises one or more of: a real time clock for time keeping, a processor, a flash memory for local data storage, a data logger for recording each spirometry test undertaken by the user, a counter for number of tests done upon each replacement of disposable resistive elements so as to provide the signal for replacement of these elements after predefined number of tests, and a transmitter for data transmission to the networked devices and applications;

In an implementation, the electronic control module triggers measurement of pressure as well as temperature at a periodic interval of at-least 10 millisecond and preferably 1 millisecond for at least allowing a derivation of exhalation as well as inhalation profile for one or more user.

In an implementation, the electronic control module is configured to record parameters involved in an inhalation-maneuveres as at least one of Peak expiratory flow rate (PEFR), Forced expiratory volume in one second (FEV1), Forced vital capacity (FVC), Forced expiratory volume in six seconds (FEV6), Forced expiratory flow during the mid 25-75% portion of the FVC (FEF-$_{25-75}$), Forced inspiratory flow volume (FIF) or other known parameters. Thereafter, the recorded parameters are processed periodically with a time-period of about 1 to 50 milliseconds to indicate correctness for each step in the actuation (inhalation or exhalation) maneuver.

In an implementation, the electronic control module is configured to determine correctness of inhalation/exhalation technique by measuring parameters corresponding to at least one of: orientation of spirometer, actuation-time; and an inhalation/exhalation flow rate profile of the user.

In an implementation, the electronic control module is configured to wirelessly communicate data pertaining to each actuation/operation of the spirometer to a remote device for further analysis.

According to an embodiment, the resistive-elements within the airway comprise a self-arranging hexagonal-stack structure and are easily removable from the airway of the device for the periodic-replacement. Further, the airway of the present electronic spirometer has two holes that are axially matched with the housing of the electronic engine. More specifically, the two holes in airways are connected through the two tubes or air-ducts with the pressure sensor of the electronic engine to allow pressure pickup at these locations in the airway. The airway itself is easily removable from the housing of the device containing the electronic engine so as to facilitate the cleaning of the housing (permitting cleaning with water) after certain number of device usage cycles (e.g. not more than 100 usage)

The present spirometer has an electronic engine that measures the pressure as well as temperature at a periodic interval of about 1 to 50 milliseconds for allowing a complete and fine determination of exhalation as well as inhalation-profile during the usage of the spirometer.

Furthermore, the present spirometer facilitates a mobile and tablet based application renderable upon a remote-device. The application in the remote-device processes the received data to continuously track the tests undertaken, time of the test, the inhalation and exhalation profile of the patient, and provides multiple reports to the patient in interactive way through user interface. The user-interface is customised for each patient based on the profile information received such as age, gender etc.

The application within the remote device for accessing the spirometer data allows the registration of multiple profiles on a single platform, thereby eliminating the possibility of inconvenience to patients such as asthmatic children, multiple family members with asthma etc. and can hence enroll multiple patients in the clinical setting.

The application may also provide information on the summary of the spirometer reading, parameters such as PEFR, $FEV_1$, FVC, $FEV_6$, FEF-$_{25-75}$, FIF or other known parameters required by the medical-practitioners. It also provides information about the correctness in number of steps in the inhalation and exhalation manoeuvre. The correctness may be displayed for each test in real time.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 4 (a and b) depict a graphical-representation depicting the accuracy in measurement of air-flow as executed by the present spirometer.

The elements in the drawings are illustrated for simplicity and may not have been necessarily been drawn to scale.

Furthermore, in terms of the construction of the device, one or more components of the device may have been represented in the drawings by conventional symbols, and the drawings may show only those specific details that are pertinent to understanding the embodiments of the present disclosure so as not to obscure the drawings with details that will be readily apparent to those of ordinary skill in the art having benefit of the description herein.

DETAILED DESCRIPTION OF FIGURES

For the purpose of promoting an understanding of the principles of the present disclosure, reference will now be made to the embodiment illustrated in the drawings and specific language will be used to describe the same. It will nevertheless be understood that no limitation of the scope of the present disclosure is thereby intended, such alterations and further modifications in the illustrated system, and such further applications of the principles of the present disclosure as illustrated therein being contemplated as would normally occur to one skilled in the art to which the present disclosure relates.

Reference throughout this specification to "an aspect", "another aspect" or similar language means that a particular feature, structure, or characteristic described in connection with the embodiment is included in at least one embodiment of the present disclosure. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary skill in the art to which this present disclosure belongs. The system, methods, and examples provided herein are illustrative only and not intended to be limiting.

Embodiments of the present disclosure will be described below in detail with reference to the accompanying drawings.

FIG. 1a illustrates an isometric view of an electronic spirometer 100, wherein said spirometer 100 is mounted upon a docking-station 200 for charging purposes, while the spirometer 100 is not in use. FIG. 1b illustrates the front view of the spirometer 100 as mounted upon the docking-station 200. Such charging-facility provides a facility to recharge the battery of the spirometer 100, thereby allowing an easy and portable-charging access and significantly reducing the possibility of misplacing the spirometer 100 when not in use. Further, the energy as obtained through charging is applied for electronic-operations like data-logging, data communication, data-analysis etc, as later explained in the figures.

Figure 1:
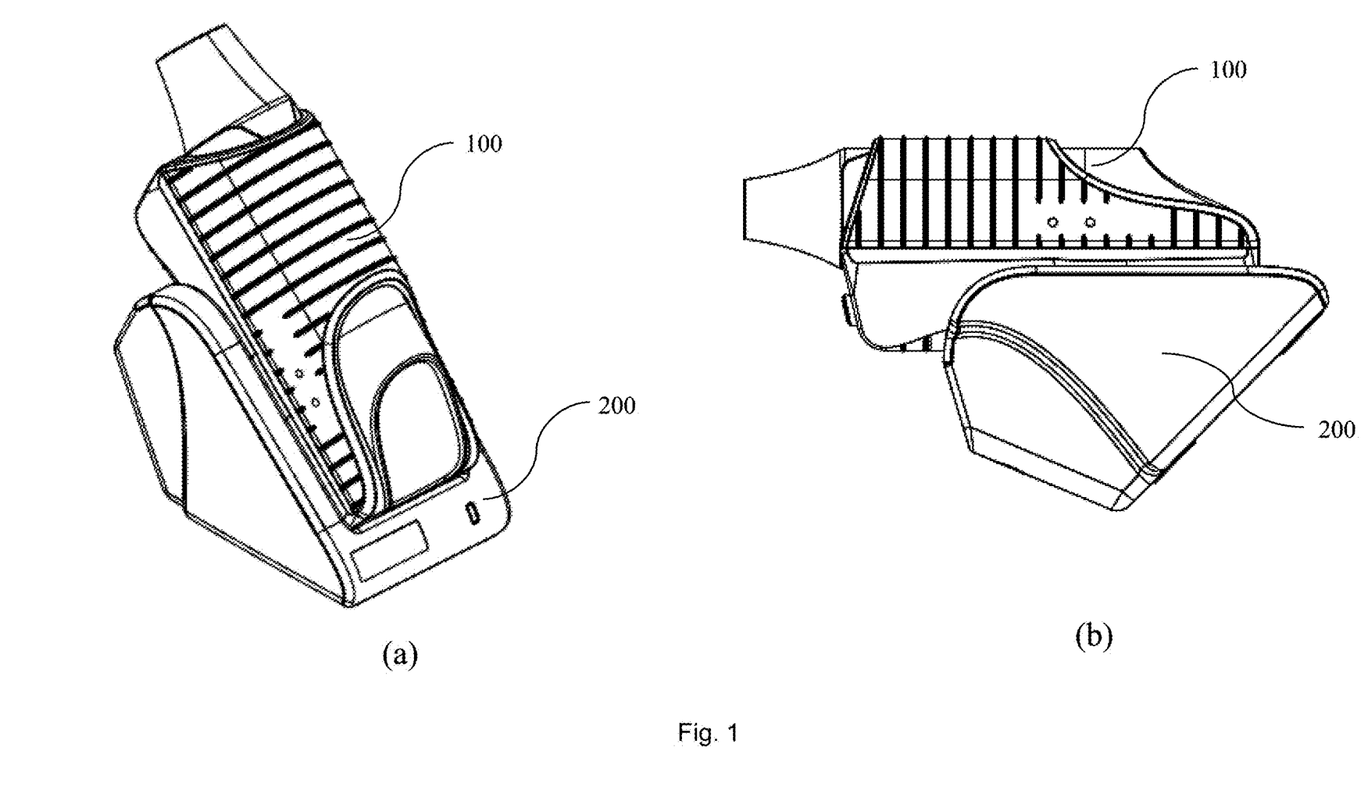
FIG. 1 illustrates an isometric view of a spirometer, in accordance with an embodiment of the present invention.
Figure 2:
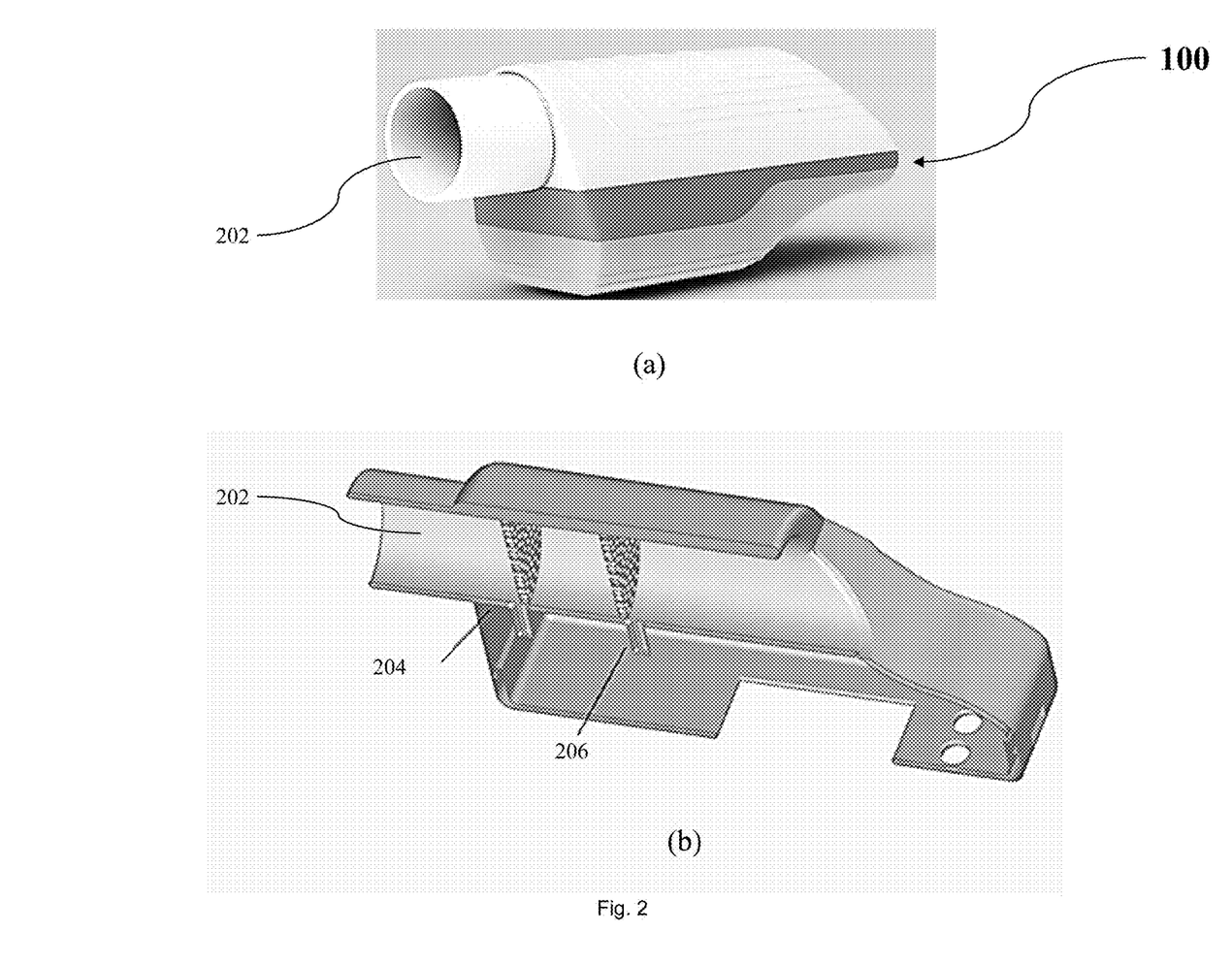
FIG. 2 illustrates a front-view and a sectional view of the airway in the spirometer as depicted in FIG. 1, in accordance with an embodiment of the present invention.

FIG. 2 illustrates a front-sectional view of the airway in the spirometer as depicted in FIG. 1, in accordance with an embodiment of the present invention. More specifically, FIG. 2a depicts an isometric-view of the spirometer 100 thereby depicting an air-passage or airway 202 therein. Such airway 202 is a hollow-tubular component, which is received in user's-mouth to enable the user at exhaling or inhaling air so as to trigger airflow parameter measurement during such exhalation and inhalation. The airway 202 or the tubular-member 202 allows an air-passage along a longitudinal-axis thereof. FIG. 2b further illustrates a sectional-view of the spirometer 100, thereby depicting an interior of the spirometer 100.

As indicated in the FIG. 2b, the resistive-elements 204 are disposed in the airflow path or airway 202. The resistive-elements 204 are at-least two disc-shaped air-resistive elements removably-arranged within the tubular member 202 to resist the air-flow. The disc-shaped resistive elements 204 are arranged within the tubular-member 202 through a snug-fit arrangement and removable therefrom.

Each of said resistive-elements 204 comprises a plurality of perforations for allowing the air-passage through the resistive-element. While each of the resistive-element 204 is a self-arranging stack, the perforations are hexagonal-holes occupying at-least about 30% of the total-area of each of the resistive-element 204 and facilitate capillary air-flow within the tubular-member. Such an arrangement ensures that a uniform and predictable pressure-drop happens across these two elements 204 at all the high and low-values of the flow rates, and thus ensures a linear-response of the pressure-drop to the flow rate in the airflow-path.

Following Table 1 depicts experimental results in terms of testing the linearity owing to the usage of hexagonal-stack elements 204 in respect of the present spirometer.

TABLE 1

Linearity advantage of hexagonal stack element

| Flow rate | Discharge Coefficient | |
| --- | --- | --- |
| [litre per minute (lpm)] | Circular stack | Hexagonal stack |
| 100 | 0.5293 | 0.5377 |
| 300 | 0.5420 | 0.5616 |
| 500 | 0.5437 | 0.5685 |
| 700 | 0.5836 | 0.5698 |
| RSD(%) | 4.23% | 2.66% |

Further, the two resistive elements 204 in the airflow-path are disposable in nature (low cost replaceable) and are easily removable from the airway 202 of the device 100 so as to facilitate their replacement after certain number of device usage cycles (e.g. usage for at least 10 times).

For such purposes of pressure-difference measurement between any two locations, at-least two locations 206 are incorporated within the airway 202. The airway 202 has two holes 206 that are axially-matched with an electronic engine (as later illustrated in FIG. 3). Such ports extend radially outwards through a wall of said tubular member 202, each of said two ports 206 are located within the tubular-member 202 near the resistive-elements 204 to cause determination of at least a pressure-difference there-between.

Further, at least a portion of the airway or tubular member 202, as provided is easily removable from the housing of the device 100, thereby facilitating an access towards the resistive-elements 204 within the tubular member 202 and allowing an ease of cleaning of housing of the electronic engine (including cleaning with water) after certain number of device usage cycles (e.g. after having had a usage of at-least 50 or 100 times).

FIG. 3 again illustrates a front-sectional view of the spirometer 100 as depicted in FIG. 1, with emphasis upon an electronic-engine 300 or an electronic control-module which forms a part of the spirometer 100 of the present subject matter.

Figure 3:
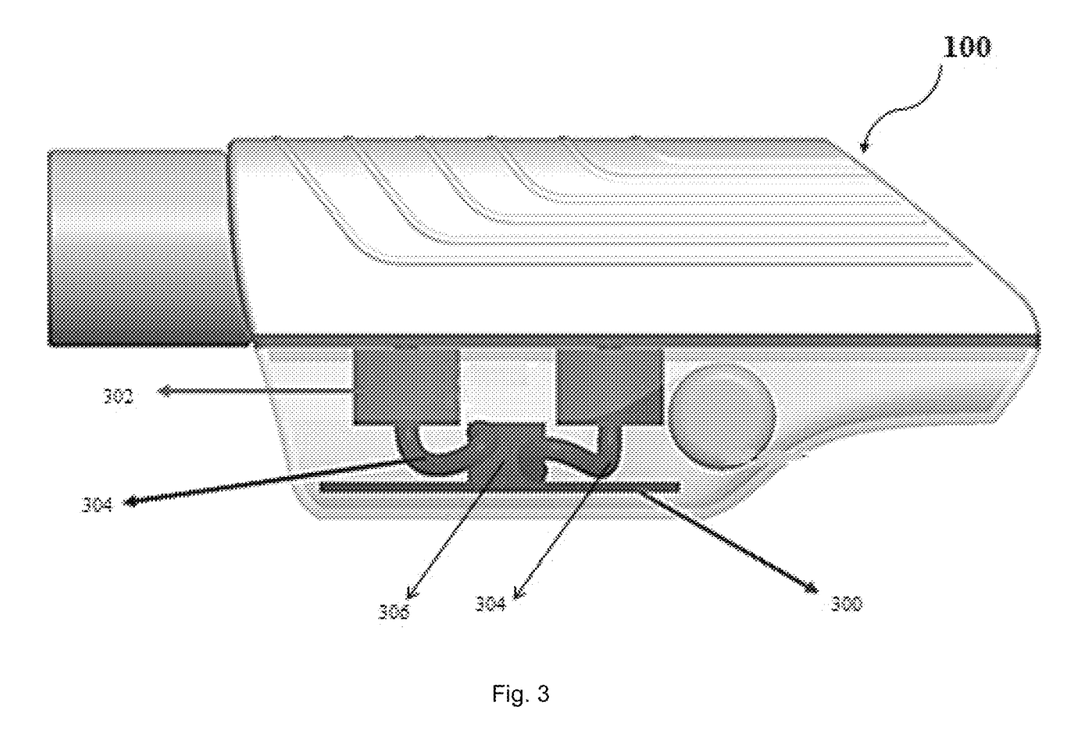
FIG. 3 illustrates a front view of electronic-engine within the spirometer as depicted in FIG. 1, in accordance with an embodiment of the present invention.

The electronic engine 300 measures pressure as well as temperature at a periodic interval in a range of about 1 to 50 milliseconds for allowing a complete and fine resolution of exhalation as well as inhalation profile during the usage of the spirometer. More specifically, the electronic engine 300 includes a pressure-sensor 306 for measuring pressure between the at least two points or locations 206 within the airway 202. In addition, the electronic engine 300 facilitates a simultaneous measurement of temperature simultaneously The points may be referred as the holes 206 (as depicted in FIG. 2) or pressure pick-off points 206. Each of said point is connected to a pressure-sensor 306 through flexible cylindrical-tubes 304 connecting the airway 202 with the pressure sensor 306. Accordingly, the two-holes 206 within the airway 202 act as pressure-pick up locations. The connection through flexible tubes 304 allows an ease of moulding, assembly, and removes chance of false pressure-pickup by the electronic-engine 300. In addition, both of the tubes 304 may be connected to the pressure pick-off points 206 through a resilient-seal 302.

Additionally, the electronic engine 300 includes a real-time clock for time keeping, flash memory for local data storage and a processor along with transmitter for data transmission to the mobile application. The electronic engine 300 enables the spirometer 100 to capture data with respect to each spirometry test undertaken by a user; determine a number of spirometry-tests conducted with respect to a particular pair of the at least two resistive-elements, and provide a signal for directing replacement of the resistive elements after occurrence of a predefined number of spirometer-tests.

Additionally, the electronic engine 300 enables recording of the parameters involved in the inhalation maneuvers including but not limited to peak expiratory flow rate (PEFR), Forced expiratory volume in one second (FEV1), Forced vital capacity (FVC), Forced expiratory volume in six seconds (FEV6), Forced expiratory flow during the mid 25-75% portion of the FVC (FEF-25-75); and Forced inspiratory flow-volume (FIF), and other known parameters.

A microprocessor (not depicted in any of the figures) within the electronic-engine 300 processes the measurement-parameters at a periodic-interval of about 1 to 50 milliseconds to validate each step in the actuation-maneuver. Additionally, parameters involved in technique monitoring such as orientation, actuation time, inhalation flow rate profile are measured and processed to compute correctness in the technique.

The spirometer 100 further deploys a low Bluetooth energy based data-transfer mechanism for transmitting the recorded data from each actuation to an application operating over a remotely located device such as a smartphone, or a tablet in respect of both Android and iOS platform. The application hosted on the remote device which uniquely identifies the spirometer 100, connects and pairs with it automatically and receives the data transmitted by the device.

Figure 4A:
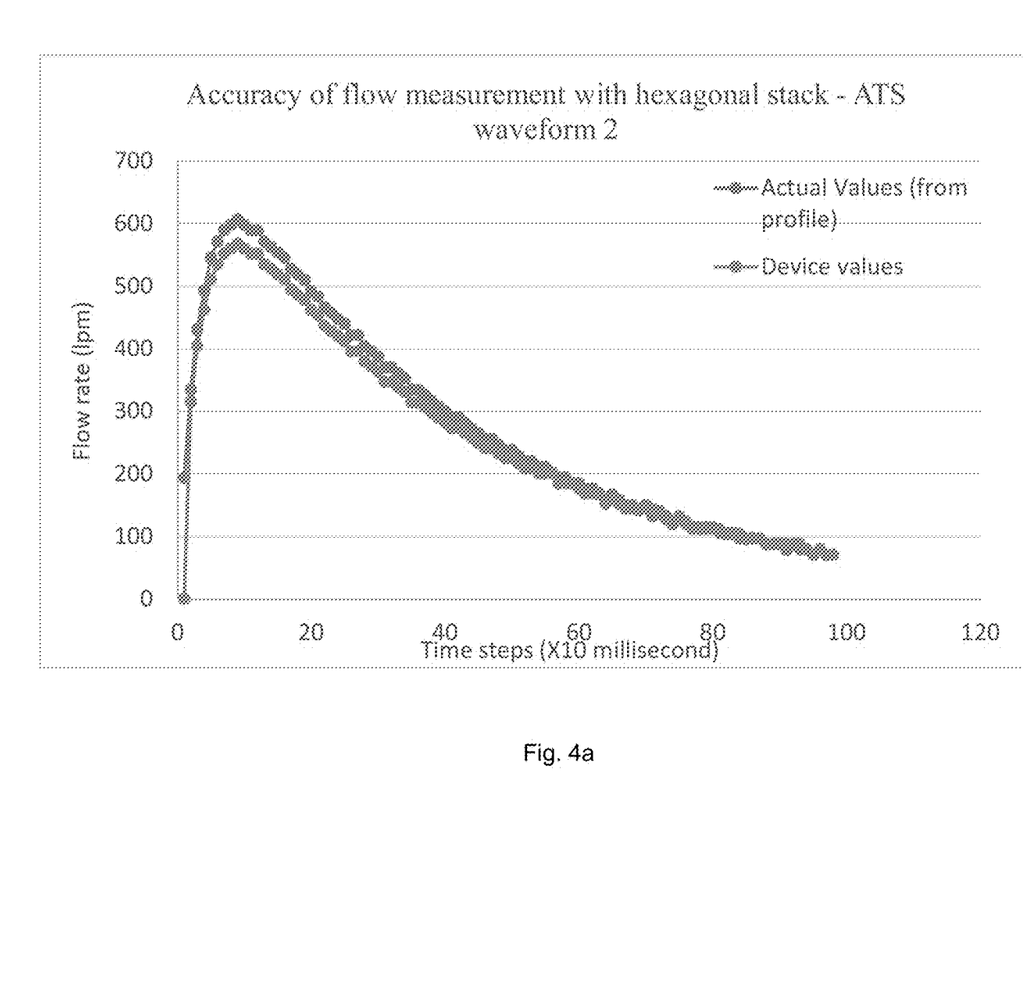
Figure 4B:
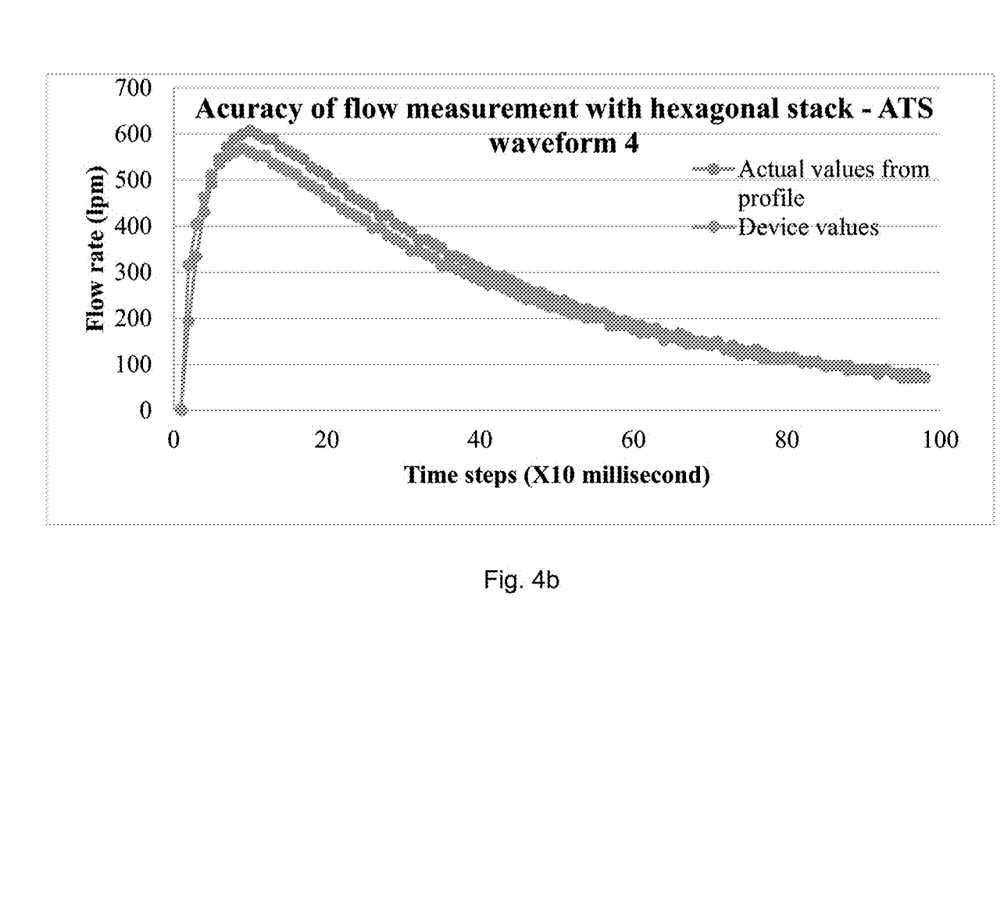

FIG. 4 (a and b) depict a graphical-representation depicting the accuracy in measurement of air-flow as executed by the spirometer 100. More specifically, as a part of experimental verification of the operation of the present device, FIG. 4 (a and b) depict a graphical representation showcasing the accuracy in measurement of air-flow as executed by the present spirometer.

As indicated in FIG. 4a, the spirometer-waveform closely follows the airflow-variation as based on actual values associated with the inhalation/exhalation profile of the user. In an example, such profiles are derived from the international ATS (American thoracic society) standards which provide 24 breathing profiles having flow rate in LPM vs time with sampling interval of 10 millisecond. Upon having increased the resolution in FIG. 4b in terms of X-axis, merely a minor deviation in the spirometer-waveforms is observed when compared with FIG. 4a.

While specific language has been used to describe the disclosure, any limitations arising on account of the same are not intended. As would be apparent to a person in the art, various working modifications may be made to the method in order to implement the inventive concept as taught herein.

It is understood that the above description is intended to be illustrative, and not restrictive. It is intended to cover all alternatives, modifications and equivalents as may be included within the spirit and scope of the invention as defined in the appended claims. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein.

Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

The invention claimed is:

1. A flow sensing arrangement within a spirometer, comprising:
a tubular-member comprising an air-passage along a longitudinal-axis thereof;
at least two disc-shaped air-resistive elements removably-arranged within the tubular member configured to resist air-flow, each of said at least two disc-shaped air-resistive elements comprising a plurality of perforations configured to allow air-passage through the at least two disc-shaped air-resistive elements; and
at least two ports extending radially outward through a wall of said tubular member, each of said at least two ports located within the tubular-member near the at least two disc-shaped air-resistive elements to permit determination of at least a pressure-difference therebetween;

an electronic control module comprising:
  a real time clock;
  memory;
  a counter; and
  a processor configured to:
    capture data with respect to each spirometry test undertaken by a user;
    determine a number of spirometry-tests conducted with respect to the at least two disc-shaped air-resistive elements based on a count of the number of spirometry test from the captured data; and
    provide a signal for directing replacement of the at least two disc-shaped air-resistive elements based on the occurrence of a pre-defined number of spirometer-tests; and
  a transmitter to transmit data processed by the processor to one or more remote- devices.

2. The arrangement as claimed in claim 1, wherein the tubular member is an elongated hollow member acting as an air-way and comprises at least one removable portion to allow access towards the at least two disc-shaped air-resistive elements within the tubular member.

3. The arrangement as claimed in claim 1, wherein the at least two disc-shaped air-resistive elements are arranged within the tubular member through a snug-fit arrangement and removable therefrom.

4. The arrangement as claimed in claim 1, wherein the plurality of perforations of the at least two disc-shaped air-resistive elements are hexagonal in shape and facilitate capillary air-flow within the tubular-member.

5. The arrangement as claimed in claim 1, wherein said at least two ports are air-pressure pick-off ports connected to a pressure-sensor through flexible-tubes to permit the determination of at least said pressure-difference between locations of the at least two disc-shaped air-resistive elements within the tubular member .

6. The arrangement as claimed in claim 1, wherein the electronic control module through the processor is configured to:
  trigger measurement of said pressure-difference and a temperature within the tubular member periodically with a time-interval ranging from 1 millisecond to 50 millisecond; and
  derive exhalation as well as inhalation profile for one or more users of the spirometer based on the measurement.

7. The arrangement as claimed in claim 1, wherein the electronic control module through the processor is configured to evaluate inhalation or exhalation subjected upon the spirometer by the user at least by measuring parameters related to one or more of:
  an orientation of the spirometer;
  actuation-time; and
  an inhalation/exhalation flow rate profile of the user.

8. The arrangement as claimed in claim 7, wherein the electronic control module through the processor and counter undertakes said measurement of parameters periodically with a time-interval of about 1 to 50 milliseconds to indicate the inhalation or exhalation as correct or incorrect.

9. The arrangement as claimed in claim 1, wherein the electronic control module through the processor is configured to capture inhalation-parameter related to at least one of:
  peak expiratory flow rate (PEFR);
  Forced expiratory volume in one second (FEV1);
  Forced vital capacity (FVC);
  Forced expiratory volume in six seconds (FEV6);
  Forced expiratory flow during the mid 25-75% portion of the FVC (FEF-25-75); and
  Forced inspiratory flow-volume (FIF).

* * * * *